(12) United States Patent
Dunman

(10) Patent No.: US 11,065,274 B2
(45) Date of Patent: Jul. 20, 2021

(54) PREVENTION AND TREATMENT FOR MICROBIAL INFECTIONS

(71) Applicant: University of Rochester, Rochester, NY (US)

(72) Inventor: Paul M. Dunman, Pittsford, NY (US)

(73) Assignee: University of Rochester, Rochester, NY (US)

(*) Notice: Subject to any disclaimer, the term of this patent is extended or adjusted under 35 U.S.C. 154(b) by 135 days.

(21) Appl. No.: 15/747,207

(22) PCT Filed: Jul. 26, 2016

(86) PCT No.: PCT/US2016/043980
§ 371 (c)(1),
(2) Date: Jan. 24, 2018

(87) PCT Pub. No.: WO2017/019657
PCT Pub. Date: Feb. 2, 2017

(65) Prior Publication Data
US 2018/0236000 A1 Aug. 23, 2018

Related U.S. Application Data

(60) Provisional application No. 62/198,325, filed on Jul. 29, 2015.

(51) Int. Cl.
*A61K 33/30* (2006.01)
*A61K 31/555* (2006.01)
*A61K 31/625* (2006.01)
*A61K 31/635* (2006.01)
*A61P 31/04* (2006.01)
*A61K 9/00* (2006.01)
*A61K 33/38* (2006.01)

(52) U.S. Cl.
CPC ............ *A61K 33/30* (2013.01); *A61K 9/0014* (2013.01); *A61K 31/555* (2013.01); *A61K 31/625* (2013.01); *A61K 31/635* (2013.01); *A61K 33/38* (2013.01); *A61P 31/04* (2018.01); *A61K 2300/00* (2013.01)

(58) Field of Classification Search
CPC ...................................... A61K 33/30
USPC ........................................................ 514/188
See application file for complete search history.

(56) References Cited

U.S. PATENT DOCUMENTS

| 6,110,908 A * | 8/2000 | Guthery ................. A01N 31/02 514/188 |
| 2010/0151029 A1* | 6/2010 | Gruening ............. A61K 9/0019 424/488 |
| 2012/0178731 A1* | 7/2012 | Guthery ................. A01N 31/02 514/188 |
| 2014/0235727 A1* | 8/2014 | Tufts ....................... A61L 15/44 514/635 |

FOREIGN PATENT DOCUMENTS

| WO | 2008/103673 A1 | 8/2008 |
| WO | WO-2008103673 A1 * | 8/2008 ............. A01N 43/54 |

OTHER PUBLICATIONS

Anderson et al., "Staphylococcal Surgical Site Infections," Infect Dis Clin N Am, 23:53-72, 2009.
Jacobs et al., "Adenylate Kinase Release as a High-Throughput-Screening-Compatible Reporter of Bacterial Lysis for Identification of Antibacterial Agents," Antimicrobial Agents and Chemotherapy, 57(1):26-36, 2013.
Kaye et al., "The Deadly Toll of Invasive Methicillin-Resistant *Staphylococcus aureus* Infection in Community Hospitals," Clinical Infectious Diseases, 46:1568-77, 2008.
Owens et al., "Surgical site infections: epidemiology, microbiology and prevention," Journal of Hospital Infection, 70(S2):3-10, 2008.
Silver et al., "Silver as biocides in bum and would dressings and bacterial resistance to silver compunds," Journal of Industrial Microbiology and Biotechnology, 33(7):627-634, 2006.
Bollenbach, "Antimicrobial interactions: mechanisms and implications for drug discovery and resistance evolution," Current Opinion in Microbiology, 2015, 27:1-9.
Brochado et al., "Species-specific activity of antibacterial drug combinations," Nature, 2018, 559:259-263.

* cited by examiner

*Primary Examiner* — Taina D Matos Negron
(74) *Attorney, Agent, or Firm* — Riverside Law LLP

(57) ABSTRACT

The present invention features a composition comprising zinc pyrithione and silver sulfiadizine, a formulation thereof and a method of treating microbial infection using the composition.

19 Claims, 8 Drawing Sheets

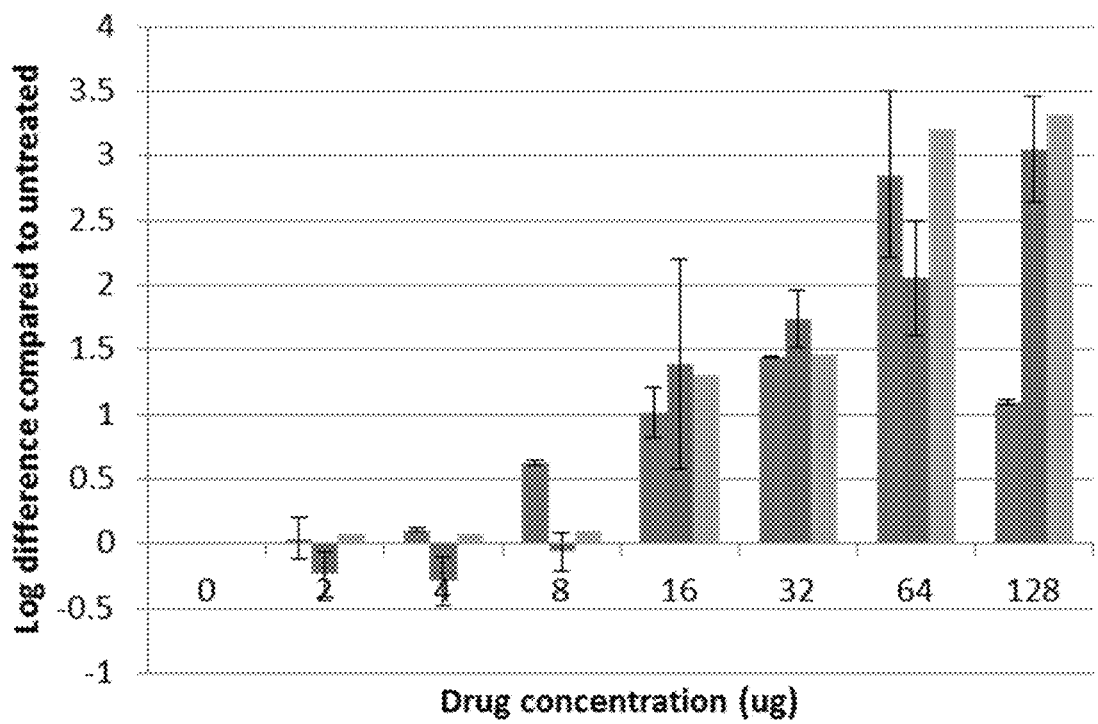
Fig. 1. Antimicrobial effects of increasing concentrations of Zinc Pyrithione (blue), Silver sulfadiazine (maroon), and the combination (green) toward 48 hr established *P. aeruginosa* biofilms. Plotted are the log-decrease in biofilm associated cells.

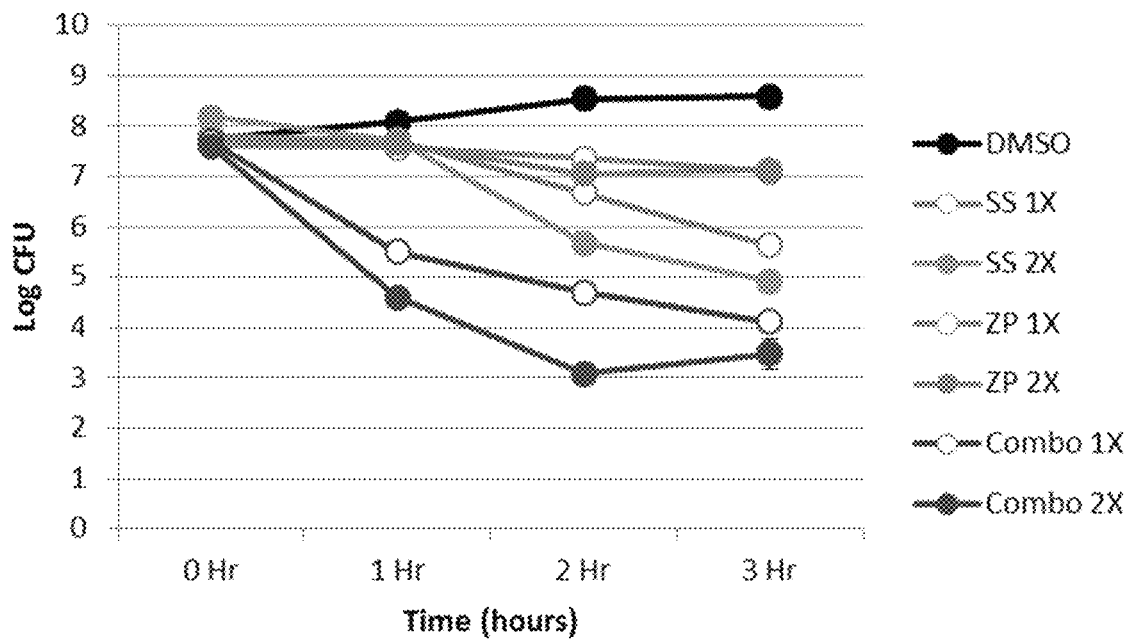
Fig. 2. Kill-curve kinetics of mock treated (DMSO), zinc pyrithione (1x and 2x minimal inhibitory concentration; blue), silver sulfadiazine (1x and 2x minimal inhibitory concentration; green), and combination of zinc pyrithione and silver sulfadiazine (red) toward *A. baumannii*.

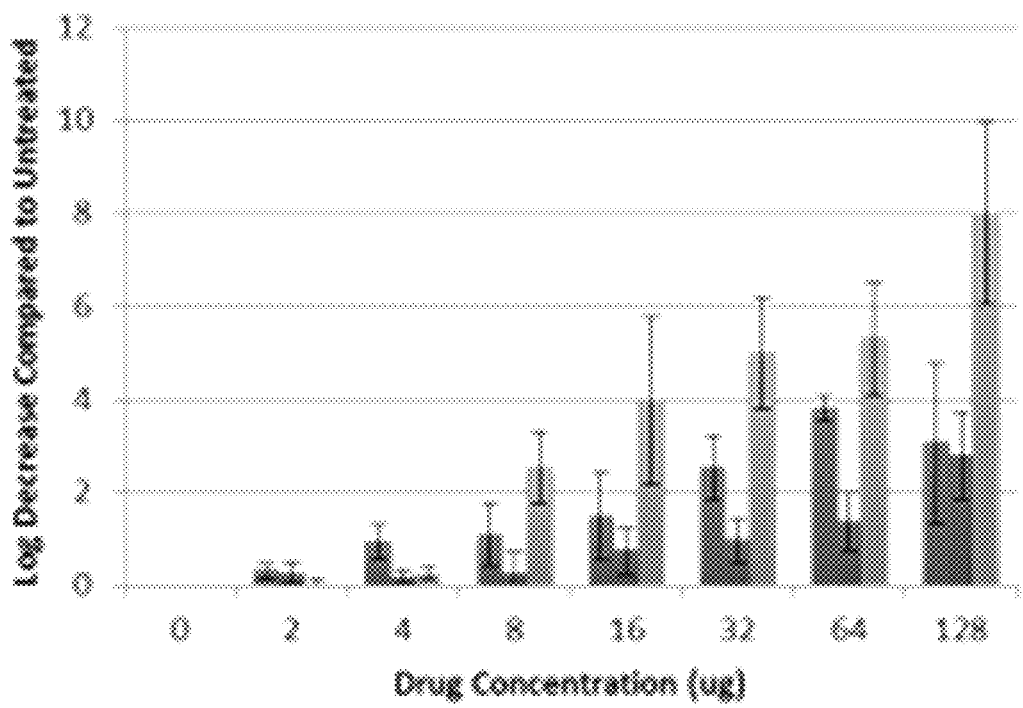
Fig. 3. Antimicrobial effects of increasing concentrations of Zinc Pyrithione (blue), Silver sulfadiazine (maroon), and the combination (green) toward 24 hr established *A. baumannii* biofilms. Plotted are the log-decrease in biofilm associated cells.

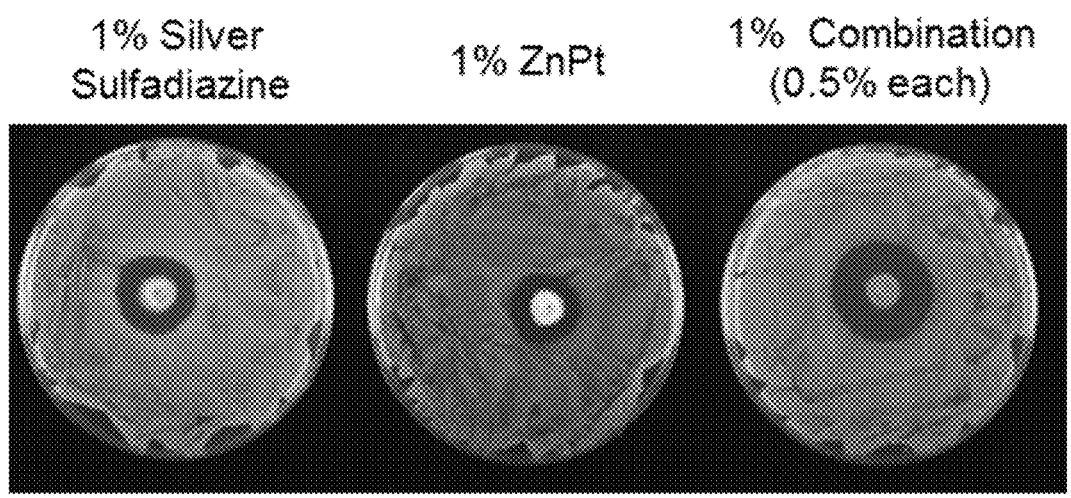
Fig. 4. Antimicrobial effects of PEG solution containing 1% silver sulfadiazine, 1% zinc pyrithione, or 1% combination (0.5% each agent) toward *A. baumannii*.

Fig. 5. Shown are the antimicrobial activity as measured by zones of inhibition (y-axis) of the indicated % concentration of either zinc pyrithione (red), silver sulfadiazine (blue) or combination (green) in PEG-ointment for *A. baumannii* (panel A), *P. aeruginosa* (panel B) and *S. aureus* (panel C).

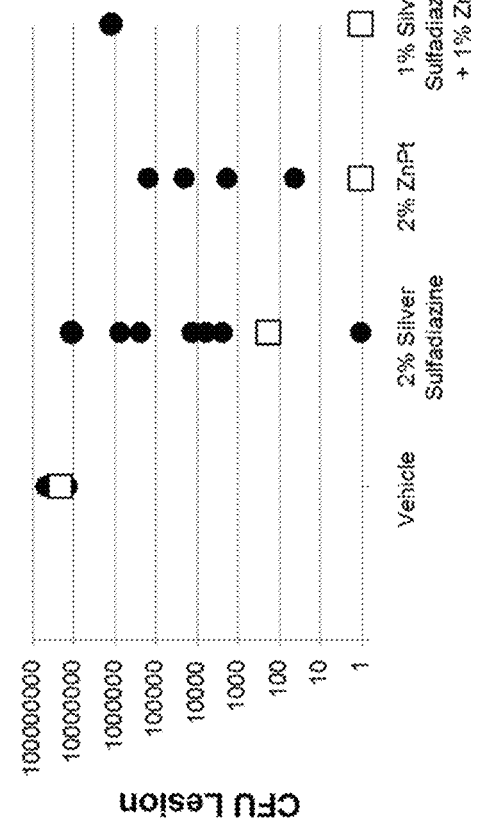
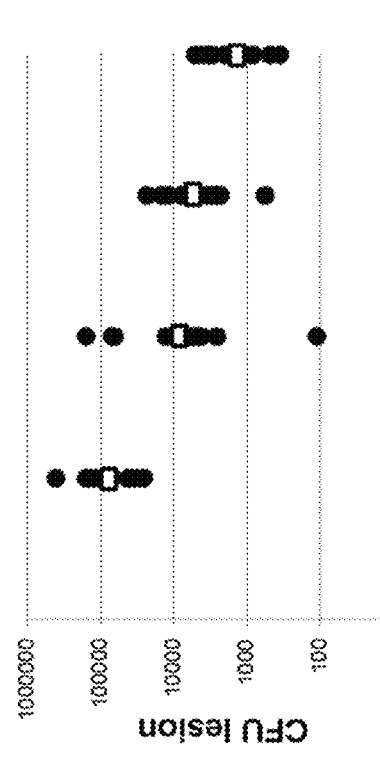
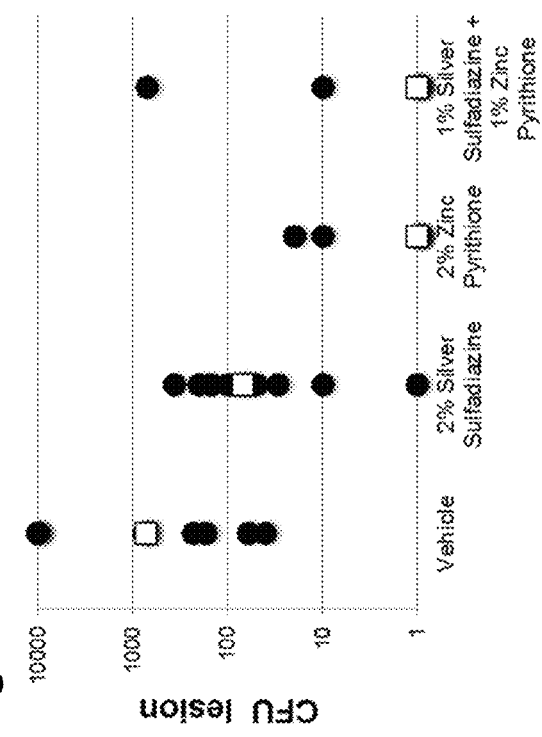
Fig. 6. Shown are murine wound burdens of *P. aeruginosa* (panel A), *S. aureus* (panel B) and *A. baumannii* (panel C) following 3 days treatment with the indicated agent. A total of 10 mice per treatment group for each organism tested. Squares indicate median measures

PREVENTION AND TREATMENT FOR MICROBIAL INFECTIONS

CROSS-REFERENCES TO RELATED APPLICATIONS

This application is a U.S. national phase application filed under 35 U.S.C. § 371 claiming benefit to International Patent Application No. PCT/US16/43980, filed Jul. 26, 2016, which is entitled to priority under 35 U.S.C. § 119(e) to U.S. Provisional Patent Application No. 62/198,325, filed Jul. 29, 2015, each of which application is hereby incorporated herein by reference in its entirety.

STATEMENT REGARDING FEDERALLY SPONSORED RESEARCH OR DEVELOPMENT

This invention was made with government support under R01AI103507 awarded by the National Institutes of Health. The government has certain rights in the invention.

FIELD

The present invention provides a composition comprising zinc pyrithione and silver sulfadiazine for the treatment of microbial infections.

BACKGROUND OF THE INVENTION

Colonization of bacteria on the surfaces of a subject or device results in serious problems including the need to vigorously treat infection conditions and/or replace the device. Considerable efforts, therefore, have been directed toward preventing or eliminating such colonization by the use of antimicrobial agents, such as antiseptics and antibiotics to prevent and/or eliminate microbial colonization. As a defense against antimicrobial agents that would affect their survival and proliferation, many surface adhered microorganisms form a dense community called biofilm. Biofilm forms on biotic and abiotic surfaces both in the environment and in the healthcare setting. In hospital wards, the formation of biofilm on vents and medical equipment enables pathogens to persist as reservoirs that can readily spread to patients. Inside the host, biofilms allow pathogens to subvert innate immune defenses and are thus associated with long-term persistence.

Silver and silver compounds have been routinely used as general antimicrobial agents for over a century. Silver, as the common ionic (active) form (Ag+), is generally recognized as a safe, broad-spectrum antimicrobial agent. It is only the ionic form that has the antimicrobial activity. Silver sulfadiazine, a substantially water insoluble compound has a combination of a weakly antibacterial sulfadiazine molecule that is complexed with silver. Silver sulfadiazine is considered a predominant burn wound treatment for the prevention and treatment of bacterial infections. However, silver sulfadiazine's efficacy can be poor. Therefore, there remains a need for treating conditions associated with microbial biofilms, for destroying or disrupting biofilms and for preventing or inhibiting or reducing biofilm formation.

SUMMARY OF THE INVENTION

The present invention provides a composition having enhanced antimicrobial efficacy and effective for inhibiting, reducing or treating microbial infections such as bacterial infections, and/or for decolonizing a microbial organism and/or for destroying, disrupting, inhibiting or reducing bacterial biofilm formation. It is our surprising and unexpected discovery that a composition comprising a combination of zinc pyrithione and silver sulfadiazine, when used to treat a microbial organism, demonstrates synergistic effect against a microbial infection or biofilm formation.

In one aspect, the present invention provides a composition comprising zinc pyrithione and silver sulfadiazine. In one embodiment, the weight ratio between zinc pyrithione and silver sulfadiazine is from about 10:1 to about 1:10. In one embodiment, the composition described herein is for topical administration to a subject. In one embodiment the subject has microbial infection. Preferably the microbial infection is characterized with microbial colonies or biofilm or biofilm formation. Preferably the microbial infection is a bacterial infection. In one embodiment, the bacteria infection is from Gram-positive or Gram-negative bacteria.

In another aspect, the present invention provides a topical formulation comprising zinc pyrithione and silver sulfadiazine and one or more pharmaceutically acceptable carriers or excipients. In one embodiment, the topical formulation comprises from about 0.001 wt. % to about 8 wt. % of zinc pyrithione per unit of the formulation. In one embodiment, the topical formulation of the present invention may take the form of a cream, a lotion, an ointment, a hydrogel, a colloid, a gel, a foam, an oil, a milk, a suspension, a wipe, a sponge, a solution, an emulsion, a paste, a patch, a pladget, a swab, a dressing, a spray and a pad.

In another aspect, the present invention provides a method of treating a microbial infection in a subject comprising administering to the subject separately, simultaneously or sequentially a therapeutically effective amount of zinc pyrithione and silver sulfadiazine. In one embodiment, the method comprises administering to the subject a therapeutically effective amount of a composition comprising zinc pyrithione and silver sulfadiazine. In one embodiment, the method comprises administering to the subject a therapeutically effective amount of a topical formulation comprising zinc pyrithione and silver sulfadiazine and one or more pharmaceutically acceptable carriers or excipients. In one embodiment, the infection is a topical infection.

In one embodiment, the present invention provides a method of decolonizing a microbial organism comprising contacting the microbial organism separately, simultaneously or sequentially with zinc pyrithione and silver sulfadiazine.

In one embodiment, the present invention provides a method of destroying or disrupting or inhibiting or reducing biofilm formation of a microbial organism comprising contacting the microbial organism separately, simultaneously or sequentially with zinc pyrithione and silver sulfadiazine.

BRIEF DESCRIPTION OF THE DRAWINGS

FIG. 1 shows antimicrobial effects of increasing concentrations of zinc pyrithione alone (first bar in each group), silver sulfadiazine alone (second bar in each group) and the combination of the two (third bar in each group) toward 48 hour established *Pseudomonas aeruginosa* biofilms. Plotted is the log-decrease in biofilm associated cells.

FIG. 2 shows kill-curve kinetics of mock treated (DMSO), zinc pyrithione (1× and 2× minimal inhibitory concentration), silver sulfadiazine (1× and 2× minimal inhibitory concentration) and combination of zinc pyrithione and silver sulfadiazine toward *Acinetobacter. baumannii*.

FIG. 3 shows antimicrobial effects of increasing concentrations of zinc pyrithione alone (first bar in each group), silver sulfadiazine alone (second bar in each group) and the combination of the two (third bar in each group) toward 24 hour established *A. baumannii* biofilms. Plotted is the log-decrease in biofilm associated cells.

FIG. 4 shows antimicrobial effects of PEG solution containing 1% silver sulfadiazine, 1% zinc pyrithione, or 1% combination (0.5% each) toward *A. baumannii*.

FIG. 5, comprising

FIG. 6, comprising FIG. 6A through FIG. 6C, shows murine wound burdens of *P. aeruginosa* (FIG. 6A), *S. aureus* (FIG. 6B) and *A. baumannii* (FIG. 6C) following three days of treatment with the indicated agent.

DETAILED DESCRIPTION

Figure 5A:
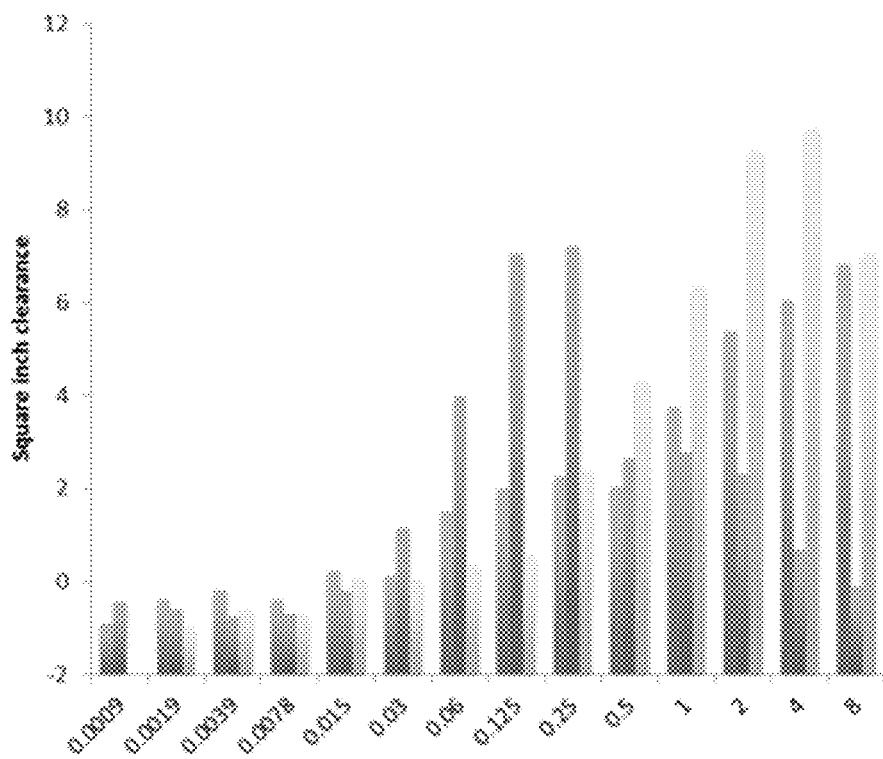
FIG. 5A through FIG. 5C, shows antimicrobial activity of either zinc pyrithione (second bar in each group), silver sulfadiazine (first bar in each group) or combination (third bar in each group) in PEG ointment for *A. baumannii* (FIG. 5A), *P. aeruginosa* (FIG. 5B) and *Staphylococcus aureus* (FIG. 5C).

For purposes of interpreting this specification, the following definitions will apply and whenever appropriate, terms used in the singular will also include the plural and vice versa.

As used herein, the term "microbial organism" or "microbe," or "microbial," or "microorganism" refers to a domain (Bacteria) of prokaryotic round, spiral, or rod-shaped single-celled, multi-celled, or a celled microorganisms that may lack cell walls or are Gram-positive or Gram-negative or alteration thereof (i.e. *Mycobacterium*) if they have cell walls, that are often aggregated into colonies or motile by means of flagella, that typically live in soil, water, organic matter, or the bodies of plants and animals, that are usually autotrophic, saprophytic, or parasitic in nutrition, and that are noted for their biochemical effects and pathogenicity. The term is intended to encompass prokaryotic or eukaryotic cells or organisms having a microscopic size and includes bacteria, viruses, archaea and eubacteria of all species as well as eukaryotic microorganisms such as yeast and fungi. The term also includes cell cultures of any species that can be cultured for the production of a biochemical. In one non-limiting example, the activity of a microbial organism can be measured by calculating the log reduction in number of the microorganism.

As used herein, the term "microbial colonization" refers to the formation of compact population groups of the same type of microorganism, such as the colonies that develop when a microbial cell begins reproducing. The microbial colonization may or may not cause disease symptoms. Decolonization refers to a reduction in the number of microbial organisms present. When the microbial organisms are completely decolonized, the microbial organisms have been eradicated and are non-detectable.

As used herein, the term "biofilm" refers to matrix-enclosed microbial accretions to biological or non-biological surfaces in which microorganisms are dispersed and/or form colonies. The biofilm typically is made of polysaccharides and other macromolecules. Biofilm formation represents a protected mode of growth that allows cells to survive in hostile environments.

As used herein, the term "biofilm formation" is intended to include the formation, growth, and modification of the microbial colonies contained with biofilm structures, as well as the synthesis and maintenance of a polysaccharide matrix of the biofilm structures. Also within the scope of this term is formation of protein-based biofilms that do not secrete polysaccharide in the matrix but which comprise proteins which permit bacteria to form biofilm architecture.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "therapeutically effective amount" of a compound of the present invention refers to an amount of the compound of the present invention that will elicit the biological or medical response of a subject, or ameliorate symptoms, slow or delay disease progression, or prevent a disease, etc. In one embodiment, the term refers to the amount that inhibits or reduces microbial colonization or infection. In one embodiment, the term refers to the amount that inhibits or reduces bacterial infection, or prevent or destroying the formation of bacterial biofilms. When applied to an individual active ingredient, administered alone, the term refers to that ingredient alone. When applied to a combination, the term refers to combined amounts of the active ingredients that result in the therapeutic effect, whether administered in combination, serially or simultaneously.

As used herein, the term "pharmaceutically acceptable carrier or excipient" refers to a carrier medium or an excipient which does not interfere with the effectiveness of the biological activity of the active ingredient(s) of the composition and which is not excessively toxic to the host at the concentrations at which it is administered. In the context of the present invention, a pharmaceutically acceptable carrier or excipient is preferably suitable for topical formulation. The term includes, but is not limited to, a solvent, a stabilizer, a solubilizer, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof. The use of such agents for the formulation of pharmaceutically active substances is well known in the art (see, for example, "Remington's Pharmaceutical Sciences", E. W. Martin, $18^{th}$ Ed., 1990, Mack Publishing Co.: Easton, Pa., which is incorporated herein by reference in its entirety).

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "topical administration" refers to the delivery to a subject by contacting the formulation directly to a surface or localized region of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition.

As used herein, the term "topical formulation" (synonymously, "topical composition") is used herein to refer to a pharmaceutical preparation intended for topical or local application to an afflicted region of a subject in need thereof, and includes such dosage forms as gel, cream, ointment, emulsion, suspension, solution, drops, lotion, paint, pessary, douche, suppository, troche, spray, sponge, film, or foam. Preferably, the topical formulation is in the form of a cream, a gel, or an ointment.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

As used herein, the term "about" refers to within 10%, preferably within 5%, and more preferably within 1% of a given value or range. Alternatively, the term "about" refers to within an acceptable standard error of the mean, when considered by one of ordinary skill in the art.

The present invention provides a composition having enhanced antimicrobial efficacy and effective for inhibiting, reducing or treating microbial infections such as bacterial infections, and/or for decolonizing a microbial organism and/or for destroying, disrupting, inhibiting or reducing bacterial biofilm formation. It is our surprising and unexpected discovery that a composition comprising a combination of zinc pyrithione and silver sulfadiazine, when used to treat a microbial organism, demonstrates synergistic effect against a microbial infection or biofilm formation. As used herein, the term "synergistic" refers to the effect obtained by combining compounds and/or agents that is greater than the effect obtained by the separate addition of each compound. The combination treatment of the present invention has shown a synergistic effect as measured by, for example, the extent of the response, the duration of response, the response rate, the stabilization rate, the duration of stabilization, the time to reduce or clear the infections, the time to eradicate the microorganisms, to that achievable on dosing one or other of the components of the combination treatment at its conventional dose. For example, the effect of the combination treatment of the present invention is synergistic because the combination treatment is therapeutically superior to the effect achievable with one component alone. Also for example, the effect of the combination treatment of the present invention is synergistic because it takes shorter time to kill the microorganisms and clear the infections. Also for example, the effect of the combination treatment of the present invention is synergistic because the combination treatment offers broader spectrum of antimicrobial activities than those with one component alone. Also for example, the effect of the combination treatment of the present invention is synergistic because one of the components in the composition described in this invention is dosed at its conventional dose and the other component(s) is/are dosed at a reduced dose and the therapeutic effect, as measured by, for example, the extent of the killing of the microorganisms such as bacteria, the time to kill the microorganisms such as bacteria, or the time to destroy or inhibit microbial colonies, or the time to disrupt or inhibit or reduce biofilm formation or growth, is equivalent to that achievable on dosing conventional amounts of the components of the combination treatment.

In one aspect, the present invention provides a composition comprising zinc pyrithione and silver sulfadiazine. In one embodiment, the weight ratio between zinc pyrithione and silver sulfadiazine is from about 10:1 to about 1:10. In one embodiment, the weight ratio between zinc pyrithione and silver sulfadiazine is from about 4:1 to about 1:4. In one embodiment, the weight ratio between zinc pyrithione and silver sulfadiazine is from about 2:1 to about 1:2. In one embodiment, the weight ratio between zinc pyrithione and silver sulfadiazine is about 1:1, about 1:2, about 1:3, about 1:4, about 1:5, about 2:1, about 3:1, about 4:1, or about 5:1. In one embodiment, the total concentration of zinc pyrithione and silver sulfadiazine in the composition of the present invention is from about 1 wt. % to about 50 wt. %. In one embodiment, the total concentration of zinc pyrithione and silver sulfadiazine in the composition of the present invention is about 50 weight percentage (wt. %), about 40 wt. %, about 30 wt. %, about 25 wt. %, about 20 wt. %, about 15 wt. %, about 10 wt. %, about 5 wt. %, about 3 wt. %, about 2 wt. %, about 1 wt. % per unit of the composition.

In one embodiment, the composition described herein is for topical administration to a subject. In one embodiment the subject has microbial infection. Preferably the microbial infection is characterized with microbial colonies or biofilm or biofilm formation. Preferably the microbial infection is a bacterial infection. In one embodiment, the bacteria infection is from Gram-positive or Gram-negative bacteria. In one embodiment the bacterial infection is from one selected from *Staphylococcus* spp., e.g. *Staphylococcus aureus, Staphylococcus epidermidis; Enterococcus* spp., e.g. *Enterococcus faecalis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp.; *Streptococcus pyogenes; Listeria* spp.; *Pseudomonas* spp.; *Mycobacterium* spp., e.g. *Mycobacterium tuberculosis; Enterobacter* spp.; *Campylobacter* spp.; *Salmonella* spp.; *Streptococcus* spp., e.g. *Streptococcus* Group A or B, *Streptoccocus pneumoniae; Helicobacter* spp., e.g. *Helicobacter pylori; Neisseria* spp., e.g. *Neisseria gonorrhea, Neisseria meningitidis; Borrelia burgdorferi; Shigella* spp., e.g. *Shigella flexneri; Escherichia coli; Haemophilus* spp., e.g. *Haemophilus influenzae; Chlamydia* spp., e.g. *Chlamydia trachomatis, Chlamydia pneumoniae, Chlamydia psittaci; Francisella fularensis; Bacillus* spp., e.g. *Bacillus anthracis; Clostridia* spp., e.g. *Clostridium botulinum; Yersinia* spp., e.g. *Yersinia pestis; Treponema* spp.; *Burkholderia* spp.; e.g. *Burkholderia mallei* and *B pseudomallei*, or the combination thereof. Preferably the infection is from one of the ESKAPE pathogens including

*Enterococcus* spp., e.g. *Enterococcus faecalis; Staphylococcus* spp., e.g. *Staphylococcus aureus, Staphylococcus epidermidis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp., or the combination thereof. Also in one embodiment, the bacteria are selected from *Acidothermus cellulyticus, Actinomyces odontolyticus, Alkaliphilus metalliredigens, Alkaliphilus oremlandii, Arthrobacter aurescens, Bacillus amyloliquefaciens, Bacillus clausii, Bacillus halodurans, Bacillus licheniformis, Bacillus pumilus, Bacillus subtilis, Bifidobacterium adolescentis, Bifidiobacterium longum, Caldicellulosiruptor saccharolyticus, Carboxydothermus hydrogenoformans, Clostridium acetobutylicum, Clostridium beijerinckii, Clostridium botulinum, Clostridium cellulolyticum, Clostridium difficile, Clostridium kluyveri, Clostridium leptum, Clostridium novyi, Clostridium perfringens, Clostridium tetani, Clostridium thermocellum, Corynebacterium diphtherias, Corynebacterium efficiens, Corynebacterium glutamicum, Corynebacterium jeikeium, Corynebacterium urealyticum, Desulfitobacterium hafniense, Desulfotomaculum reducens, Eubacterium ventriosum, Exiguobacterium sibiricum, Finegoldia magna, Geobacillus kaustophilus, Geobacillus thermodenitrificans, Janibacter* sp., *Kineococcus radiotolerans, Lactobacillus fermentum, Listeria monocytogenes, Listeria innocua, Listeria welshimeri, Moorella thermoacetica, Mycobacterium avium, Mycobacterium bovis, Mycobacterium gilvum, Mycobacterium leprae, Mycobacterium paratuberculosis, Mycobacterium smegmatis, Mycobacterium tuberculosis, Mycobacterium ulcerans, Mycobacterium vanbaalenii, Nocardioides* sp., *Nocardia farcinica, Oceanobacillus iheyensis, Pelotomaculum the rmopropionicum, Rhodococcus* sp., *Saccharopolyspora erythraea,* coagulase-negative *Staphylococcus* species, *Staphylococcus aureus,* methicillin resistant *Staphylococcus aureus* (MRSA), *Staphylococcus epidermidis,* methicillin resistant *Staphylococcus epidermidis,* (MRSE), *Staphylococcus pseudintermedius, Staphylococcus intermedius, Staphylococcus delphini, Streptococcus agalactiae, Streptococcus gordonii, Streptococcus mitis, Streptococcus oralis, Streptococcus pneumoniae, Streptococcus sanguinis, Streptococcus suis, Streptomyces avermitilis, Streptomyces coelicolor, Thermoanaerobacter ethanolicus, Thermoanaerobacter tengcongensis,* or the combination thereof.

In another aspect, the present invention provides a topical formulation comprising zinc pyrithione and silver sulfadiazine and one or more pharmaceutically acceptable carriers or excipients. In one embodiment, the topical formulation comprises from about 0.001 wt. % to about 8 wt. % of zinc pyrithione per unit of the formulation. In one embodiment, the topical formulation comprises from about 0.001 wt. % to about 8 wt. % of silver sulfadiazine per unit of the formulation. In one embodiment, the topical formulation comprises from about 0.001 wt. % to about 8 wt. % of zinc pyrithione and from about 0.001 wt. % to about 8 wt. % of silver sulfadiazine per unit of the formulation. In one embodiment, the topical formulation comprises from about 0.001 wt. % to about 4 wt. % of zinc pyrithione and from about 0.001 wt. % to about 4 wt. % of silver sulfadiazine per unit of the formulation. In one embodiment, the topical formulation comprises from about 0.015 wt. % to about 0.5 wt. % of zinc pyrithione and from about 0.015 wt. % to about 2 wt. % of silver sulfadiazine per unit of the formulation. In one embodiment, the topical formulation comprises one selected from about 0.25 wt. %, about 0.5 wt. %, or about 1 wt. % of zinc pyrithione and one selected from about 0.25 wt. %, about 0.5 wt. %, or about 1 wt. % of silver sulfadiazine per unit of the formulation.

In one embodiment, the topical formulation of the present invention comprises from about 0.001 wt. % to about 8 wt. % of zinc pyrithione, from about 0.001 wt. % to about 8 wt. % of silver sulfadiazine and about 10:1 to about 1:10 weight ratio between zinc pyrithione and silver sulfadiazine per unit of the formulation. In one embodiment, the topical formulation of the present invention comprises from about 0.001 wt. % to about 4 wt. % of zinc pyrithione, from about 0.001 wt. % to about 4 wt. % of silver sulfadiazine and about 4:1 to about 1:4 weight ratio between zinc pyrithione and silver sulfadiazine per unit of the formulation. In one embodiment, the topical formulation of the present invention comprises from about 0.015 wt. % to about 0.5 wt. % of zinc pyrithione, from about 0.015 wt. % to about 0.5 wt. % of silver sulfadiazine and about 2:1 to about 1:2 weight ratio between zinc pyrithione and silver sulfadiazine per unit of the formulation.

In one embodiment, the topical formulation of the present invention may take the form of a cream, a lotion, an ointment, a hydrogel, a colloid, a gel, a foam, an oil, a milk, a suspension, a wipe, a sponge, a solution, an emulsion, a paste, a patch, a pladget, a swab, a dressing, a spray and a pad.

The topical formulation of the present invention comprises one or more pharmaceutically acceptable carrier. Examples of the pharmaceutically acceptable carriers that are usable in the context of the present invention include carrier materials such as a solvent, a stabilizer, a solubilizer, a filler, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof.

Examples of solvents are water or purified water, alcohols (e.g., ethanol, benzyl alcohol), vegetable, marine and mineral oils, polyethylene glycols, propylene glycols, glycerol, and liquid polyalkylsiloxanes.

Inert diluents or fillers may be sucrose, sorbitol, sugar, mannitol, microcrystalline cellulose, starches, calcium carbonate, sodium chloride, lactose, calcium phosphate, calcium sulfate, or sodium phosphate.

Examples of buffering agents include citric acid, acetic acid, lactic acid, hydrogenophosphoric acid, diethylamine, sodium hydroxide and tromethane (/.e., tris(hydroxymethyl) aminomethane hydrochloride).

Suitable suspending agents are, for example, naturally occurring gums (e.g., acacia, arabic, xanthan, and tragacanth gum), celluloses (e.g., carboxymethyl-, hydroxyethyl-, hydroxypropyl-, and hydroxypropylmethyl-cellulose), alginates and chitosans.

Examples of dispersing or wetting agents are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to a topical composition of the invention to prevent microbial contamination that can affect the stability of the formulation and/or cause infection in the patient. Suitable examples of preservatives include parabens (such as methyl, ethyl, propyl, /p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol.

Examples of chelating agents include sodium EDTA and citric acid.

Examples of gel bases or viscosity-increasing agents are liquid paraffin, polyethylene, fatty oils, colloidal silica or aluminum, glycerol, propylene glycol, propylene carbonate, carboxyvinyl polymers, magnesium-aluminum silicates, hydrophilic polymers (such as, for example, starch or cellulose derivatives), water-swellable hydrocolloids, carragenans, hyaluronates, alginates, and acrylates.

Ointment bases suitable for use in the compositions of the present invention may be hydrophobic or hydrophilic, and include paraffin, lanolin, liquid polyalkylsiloxanes, cetanol, cetyl palmitate, vegetal oils, sorbitan esters of fatty acids, polyethylene glycols, and condensation products between sorbitan esters of fatty acids, ethylene oxide (e.g., polyoxyethylene sorbitan monooleate), polysorbates, white petrolatum and white wax.

Examples of humectants are ethanol, isopropanol glycerin, propylene glycol, sorbitol, lactic acid, and urea. Suitable emollients include cholesterol and glycerol.

Examples of skin protectants include vitamin E, allatoin, glycerin, zinc oxide, vitamins, and sunscreen agents.

Thickening agents are generally used to increase viscosity and improve bioadhesive properties of pharmaceutical or cosmetic compositions. Examples of thickening agents include, but are not limited to, celluloses, polyethylene glycol, polyethylene oxide, naturally occurring gums, gelatin, karaya, pectin, alginic acid, povidone, and Carbopol® polymers. Particularly interesting are thickening agents with thixotropic properties (i.e., agents whose viscosity is decreased by shaking or stirring). The presence of such an agent in a composition allows the viscosity of the composition to be reduced at the time of administration to facilitate its application to the skin and, to increase after application so that the composition remains at the site of administration.

Bioadhesive polymers are useful to hydrate the skin and enhance its permeability. Bioadhesive polymers can also function as thickening agents. Examples of bioadhesive polymers include, but are not limited to, pectin, alginic acid, chitosan, polysorbates, poly(ethyleneglycol), oligosaccharides and polysaccharides, cellulose esters and cellulose ethers, and modified cellulose polymers.

Permeation enhancing agents are vehicles containing specific agents that affect the delivery of active components through the skin. Permeation enhancing agents are generally divided into two classes: solvents and surface active compounds (amphiphilic molecules). Examples of solvent permeation enhancing agents include alcohols (e.g., ethyl alcohol, isopropyl alcohol), dimethyl formamide, dimethyl acetamide, dimethyl sulfoxide, 1-dodecylazocycloheptan-2-one, N-decyl-methylsulfoxide, lactic acid, N,N-diethyl-m-toluamide, N-methyl pyrrolidone, nonane, oleic acid, petrolatum, polyethylene glycol, propylene glycol, salicylic acid, urea, terpenes, and trichloroethanol. Surfactant permeation enhancing agents may be nonionic, amphoteric, cationic, or zwitterionic. Suitable nonioinic surfactants include poly(oxyethylene)-poly(oxypropylene) block copolymers, commercially known as poloxamers; ethoxylated hydrogenated castor oils; polysorbates, such as Tween 20 or Tween 80. Amphoteric surfactants include quaternized imidazole derivatives, cationic surfactants include cetypyridinium chloride, and zwitterionic surfactants include the betaines and sulfobetaines. Other examples of suitable permeation enhancers include pentadecalactone, 2-pyrrolidine, 1-dodecal-azacycloheptane-2-one, calcium thioglycolate, hexanol, derivatives of 1,3-dioxanes (i.e., 1,3-dioxacyclohexanes) and 1,3-dioxalanes (i.e., 1,3-dioxacyclopentanes), 1-N-dodecyl-2-pyrrolidone-5-carboxylic acid, 2-pentyl-2-oxo-pyrrolidineacetic acid, 2-dodecyl-2-oxo-1-pyrrolidineacetic acid, and 1-azacycloheptan-2-one-2-dodecylacetic acid among others.

In another aspect, the present invention provides a method of treating a microbial infection in a subject comprising administering to the subject separately, simultaneously or sequentially a therapeutically effective amount of zinc pyrithione and silver sulfadiazine. In one embodiment, the method comprises administering to the subject a therapeutically effective amount of a composition comprising zinc pyrithione and silver sulfadiazine. In one embodiment, the method comprises administering to the subject a therapeutically effective amount of a topical formulation comprising zinc pyrithione and silver sulfadiazine and one or more pharmaceutically acceptable carriers or excipients, wherein the pharmaceutically acceptable carriers or excipients are defined herein throughout the specification. In one embodiment, the infection is a topical infection. The topical infection is an infection on a surface or localized region of a subject including skin, eye, a mucous membrane, a surface of cavity, etc. In one embodiment, the topical infection is the infection on the skin. In one embodiment, the topical infection is in the form of wound, ulcer and lesion. According to any of the methods described herein, the microbial organism is a bacterium. Preferably the bacterium is one selected from the ESKAPE pathogens including *Enterococcus* spp., e.g. *Enterococcus faecalis, Staphylococcus* spp., e.g. *Staphylococcus aureus, Staphylococcus epidermidis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp., or the combination thereof.

In one embodiment, the present invention provides a method of decolonizing a microbial organism comprising contacting the microbial organism separately, simultaneously or sequentially with zinc pyrithione and silver sulfadiazine. In one embodiment, the method comprises contacting the microbial organism with a composition comprising zinc pyrithione and silver sulfadiazine. In one embodiment, the method comprises contacting the microbial organism with a topical formulation comprising zinc pyrithione and silver sulfadiazine and one or more pharmaceutically acceptable carriers or excipients, wherein the pharmaceutically acceptable carriers or excipients are defined herein throughout the specification. According to any of the methods describes herein, the microbial organism is a bacterium. Preferably the bacterium is one selected from the ESKAPE pathogens including *Enterococcus* spp., e.g. *Enterococcus faecalis, Staphylococcus* spp., e.g. *Staphylococcus aureus, Staphylococcus epidermidis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp., or the combination thereof.

In one embodiment, the present invention provides a method of destroying or disrupting or inhibiting or reducing biofilm formation of a microbial organism comprising contacting the microbial organism separately, simultaneously or sequentially with zinc pyrithione and silver sulfadiazine. In one embodiment, the method comprises contacting the microbial organism with a composition comprising zinc pyrithione and silver sulfadiazine. In one embodiment, the method comprises contacting the microbial organism with a topical formulation comprising zinc pyrithione and silver sulfadiazine and one or more pharmaceutically acceptable carriers or excipients, wherein the pharmaceutically acceptable carriers or excipients are defined herein throughout the specification. According to any of the methods describes herein, the microbial organism is a bacterium. Preferably the bacterium is one selected from the ESKAPE pathogens including *Enterococcus* spp., e.g. *Enterococcus faecalis, Staphylococcus* spp., e.g. *Staphylococcus aureus, Staphylococcus epidermidis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp., or the combination thereof.

Accordingly the present invention provides the use of zinc pyrithione and silver sulfadiazine for treating a microbial infection, or for decolonizing a microbial organism, or for destroying or disrupting or inhibiting or reducing biofilm formation of a microbial organism.

Accordingly the present invention provides the use of a combination comprising zinc pyrithione and silver sulfadiazine for treating a microbial infection, or for decolonizing a microbial organism, or for destroying or disrupting or inhibiting or reducing biofilm formation of a microbial organism.

Accordingly the present invention provides the use of a topical formulation for treating a microbial infection, or for decolonizing a microbial organism, or for destroying or disrupting or inhibiting or reducing biofilm formation of a microbial organism, said topical formulation comprises zinc pyrithione and silver sulfadiazine and one or more pharmaceutically acceptable carriers or excipients.

The combination therapy of the present invention may be performed alone or in conjunction with another therapy. For example, the combination therapy of the present invention may be used in conjunction with a disinfectant, antiseptic, antibiotic, or biocide on a surface such as medical devices and indwelling devices including stents, catheters, peritoneal dialysis tubing, draining devices, joint prostheses, dental implants and the like.

By way of examples below, the present invention provides a synergistic combination therapy comprising zinc pyrithione and silver sulfadiazine that can be administered topically for the treatment of a microbial infection. Reference is now made to the following examples, which together with the above descriptions illustrate some embodiments of the invention in a non-limiting manner.

EXAMPLES

*Pseudomonas aeruginosa, Staphylococcus aureus* and *Acinetobacter baumannii* are notoriously difficult to treat bacterial pathogens that are common causes of persistent skin and soft tissue wound infections in post-operative-, burn-, and dialysis-patient populations. While such infections can be debilitating on their own-right they often lead to invasive disease and corresponding increased rates of morbidity and mortality. For instance, methicillin resistant *S. aureus* (MRSA) has been reported to account for 7-30% burn wound infections and 15-20% of surgical site infections (Anderson and Kaye, 2009, Infect Dis Clin North Am, 23 (1): 53-72; Owens and Stoessel, 2008, J Hosp Infect, 70 Suppl 2: 3-10) that lead to a 1-year mortality rate of 21.7% in certain patient populations (Kaye et al., 2008, Clin Infect Dis, 46 (10): 1568-77).

Disease onset frequently begins once these organisms breaching the skin's protective barrier, followed by colonization of the underlying tissue, and ultimately dissemination. While *S. aureus, P. aeruginosa* and *A. baumannii* are difficult to treat due to the emergence of antibiotic resistance that negates the antimicrobial effects of first-line antibiotics, even susceptible strains are problematic and difficult to eradicate in the wound setting. Several lines of evidence suggest that this can be attributed to the formation of biofilm-associated growth state in the wound site. We set out to identify agents that display bactericidal activity toward bacterial pathogens when they were in the biofilm growth state—such agents would have tremendous promise as wound infection therapeutics.

Example 1

Zinc Pyrithione Exhibits Antimicrobial Activity Toward Established *P. Aeruginosa* Biofilm-Associated Cells Members of the Selleck compound library were screened (50 μM) for agents that displayed bactericidal activity toward 48 hour *P. aeruginosa* biofilms using the adenylate kinase assay, as previously described (Jacobs et al., *Antimicrob Agents Chemother*, 57 (1): 26-36 (2013)). Results of that campaign identified that the antimicrobial agent, zinc pyrithione (ZnPt), was among the best performer. Dose response testing confirmed that 50 μM (15.8 μg ml$^{-1}$) treatment resulted in a 1-log reduction in biofilm associated *Pseudomonas aeruginosa* (FIG. 1). Further, at low concentrations (4 to 64 μg ml$^{-1}$) the agent's antibiofilm activity toward *P. aeruginosa*, was comparable to that of silver sulfadiazine, which is commonly used for the therapeutic intervention of wound site infections.

Example 2

Zinc Pyrithione Displays Broad Spectrum Antimicrobial Activity

As a means to further characterize the agent's antimicrobial activity its efficacy toward other members of the ESKAPE pathogens were evaluated and compared to sulfadiazine (Table 1; below). Standard minimum inhibitory concentration testing revealed that ZnPt displayed greater antimicrobial activity toward

| Bacterial Species | Strain | ZnPt MIC (ug/ml) | Ag Sulfadiazine MIC (ug/ml) |
|---|---|---|---|
| *Escherichia coli* | 8307 | 1 | 16 |
| *Staphylococcus aureus* | UAMS-1 | 2 | 16 |
| *Klebsiella pneumoniae* | CKP4 | 2 | 16 |
| *Acinetobacter baumannii* | 983709 | 2 | 4 |
| *Pseudomonas aeruginosa* | PA01 | 16 | 8 |
| *Enterococcus faecium* | 824-05 | 2 | 8 |
| *Enterococcus faecalis* | V583 | 2 | 8 |
| *Enterobacter cloacae* | Clinical Isolate | 4 | 16/32 |

*Escherichia coli* (1 μg ml$^{-1}$) and the ESKAPE pathogens *Enterococcus faecium* (2 μg ml$^{-1}$), *Staphylococcus aureus* (2 μg ml$^{-1}$), *Klebsiella pneumoniae* (2 μg ml$^{-1}$), *Acinetobacter baumannii* (2 μg ml$^{-1}$), and *Enterobacter cloacae* (4 μg ml$^{-1}$), in comparison to silver sulfadiazine. Conversely, ZnPt exhibited reduced activity toward planktonic *P. aeruginosa*

(16 µg ml$^{-1}$). Taken together, we considered that a combination therapeutic consisting of ZnPt+silver sulfadazine may have broader spectrum activity than either agent alone.

As a first test of that possibility, fractional inhibitory index concentration (FIC) measures were performed to establish whether the combination were compatible. Interestingly, the combination demonstrated FIC measures of 0.5-0.75 for *P. aeruginosa*, *A. baumannii* and *S. aureus*, indicating an advantage. As shown in FIG. 2, kill curve analyses indicated that this effect could, in part, be attributed to more rapid killing activity of the combination in comparison to either agent by itself.

Example 3

Zinc Pyrithione and Silver Sulfadiazine Combination Display Improved Activity Toward *A. baumannii* and *S. aureus* Biofilms Despite their additive effects toward planktonic *P. aeruginosa*, combinations of ZnPt+Silver sulfadiazine had no significant benefit or antagonistic effects toward the organism when in the biofilm state, in comparison to either agent alone (FIG. 1.). Conversely, combination treatment was more effective than either agent (alone) at reducing biofilm-associated *A. baumannii* and *S. aureus* (representative results for *A. baumannii* are shown in FIG. 3). More specifically while ZnPt displayed improved activity toward *A. baumannii* biofilms in comparison to silver sulfadiazine alone, combination treatment with both agents exhibited the greatest antibiofilm activity, resulting in a 4-log reduction in bacteria at combination concentrations ≥16 µg ml$^{-1}$. This is perhaps best exemplified at the highest concentration tested (128 µg ml$^{-1}$); both agents individually resulted in an average of 3.5-log reduction whereas the combination (64 µg ml$^{-1}$ of each agent) essentially eliminated all biofilm associated *A. baumannii* (8-log reduction).

Example 4

ZnPt+Silver Sulfadiazine Combination Topical Formulations

As a prerequisite to animal antimicrobial efficacy testing we set out to determine whether the ZnPt+silver sulfadiazine could be formulated into a topical for wound efficacy measures. In that regard, polyethylene (PEG)-based vehicles are commonly used for such purposes thus we set out to measure the performance of each agent. As shown in FIG. 4, both agents (individually) exhibited antimicrobial activity toward *A. baumannii*, *S. aureus* and *Pseudomonas aeruginosa*, indicating that the PEG-formulation did not adversely affect either compound. Further, the combination also appeared to display antimicrobial activity that exceeded each agent alone.

Figure 5B:
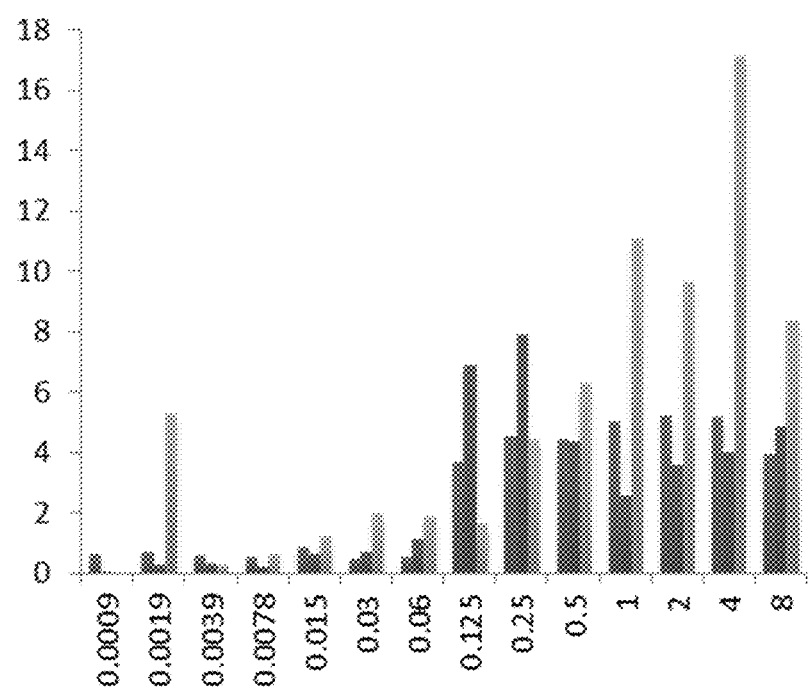
Figure 5C:
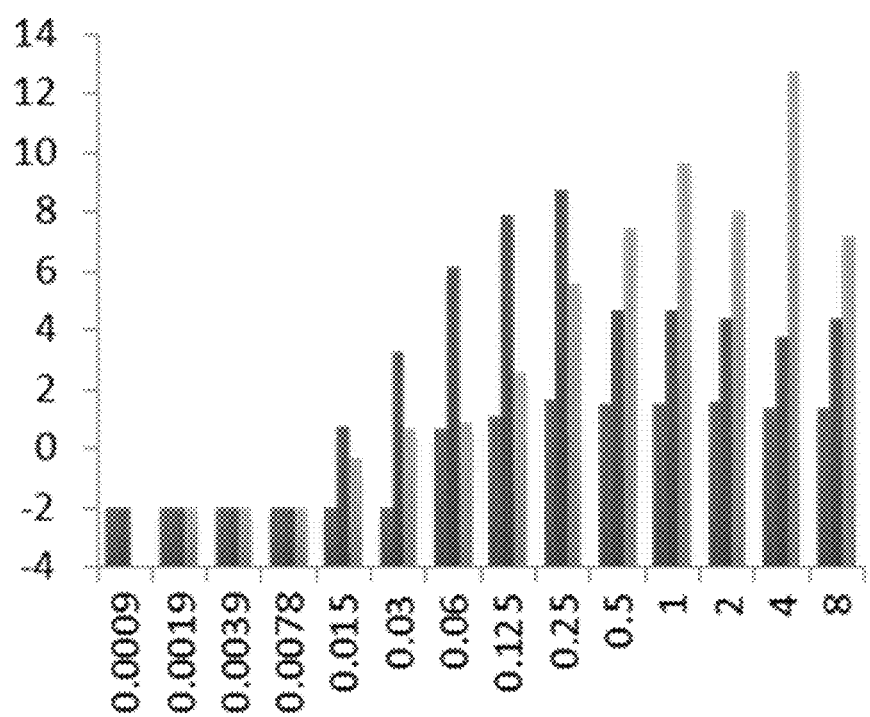
Figure 7:
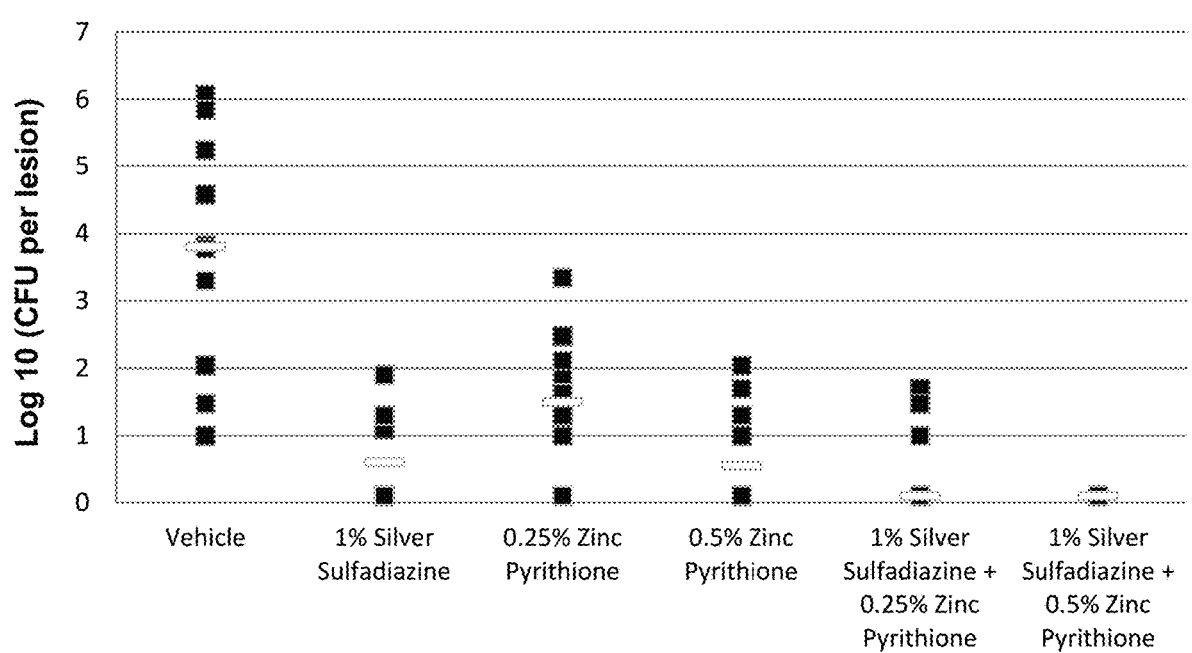
FIG. 7 shows dose responsiveness of the combination containing zinc pyrithione and silver sulfadiazine.

Dose response measures of the antimicrobial activity of various concentrations (0 to 8% active agent) were used to define the optimal concentration of each agent alone and in combination. As shown in FIG. 5, at low concentrations (~0.015 to 0.25%) ZnPt displayed a dose-dependent increase in antimicrobial activity against *A. baumannii*, *S. aureus* and *P. aeruginosa*. At concentrations ≥0.5% activity decreased but was maintained up to ~2% for all organisms. Conversely, silver sulfadiazine was relatively unactive at concentrations below 0.06% to 0.125% of the agent, whereas a dose-dependent increase in activity toward *A. baumannii*. The compound's activity toward *S. aureus* and *P. aeruginosa* differed, here a dose-dependent increase in activity beyond was not observed.

The combination of ZnPt+silver sulfadiazine displayed a similar dose-response for all organisms tested. Antimicrobial activity increased in a dose dependent manner between 0.015% to 4% active ingredients) then decreased at the highest concentration tested (8%), with maximal antimicrobial activity observed between 1% (0.5% each agent) to 4% (2% each agent). In the clinical setting Silver sulfadiazine is commonly used at 2% concentration but, like ZnPt, is known to exhibit high concentration cytotoxicity and consequently requires strict dosing regiments to achieve an antimicrobial efficacy/wound healing balance. Accordingly, we considered that 2% of the combination (1% each agent) could approach the maximal dose at which efficacy may be seen in mice and allow direct comparison of silver sulfadiazine use in the clinical setting (control).

Example 5

Antimicrobial Efficacy Toward *P. Aeruginosa*, *A. Baumannii* and *S. Aureus* Models of Murine Wound Infection Using a murine model of wound infection, the antimicrobial efficacy of vehicle (PEG), 2% silver sulfadiazine, 2% zinc pyrithione and 2% combination (1% silver sulfadiazine+1% zinc pyrithione) was compared using *A. baumannii*, *S. aureus* or *P. aeruginosa*. Treatments were twice a day for a total of three days, at which point the wound bacterial burden was measured.

As shown in FIG. 6A, vehicle treated *P. aeruginosa* displayed approximately 1×10$^6$ cfu per wound following 3 day administration. Silver sulfadiazine (alone) and ZnPt (alone) treatment resulted in a 1-log and 1.2-log decrease in bacterial burden following treatment, respectively. The combination therapy displayed the greatest efficacy (1.8-log), indicating that the combination exhibits a mild increase in activity toward the organism during these conditions. Studies of *A. baumannii* and *S. aureus* were much more impressive. As shown in FIG. 6B. *S. aureus* burden was decreased significantly by 2% silver sulfadiazine, but 6 out of 10 animals were not cleared of the organism. Conversely, 6 and 9 (of 10) were completed cleared of *S. aureus* following 3 day testing with 2% zinc pyrithione and 2% combination (1% silver sulfadiazine and 1% zinc pyrithione), respectively. Likewise, the combination of 1% silver sulfadiazine+ 1% ZnPt nearly eradicated *A. baumannii* from all animals, whereas the effects of current standard treatment (2% silver sulfadiazine) where only modest; FIG. 6C).

To evaluate the dose responsiveness of the combination and whether lower concentrations of ZnPt are equally as effective as 1% zinc pyrithione, lower concentrations (0.25-0.5%) zinc pyrithione were dosed alone and in combination with 1% silver sulfadiazine toward *A. baumannii* in vivo. Surprisingly, results revealed that the efficacy of 1% silver sulfadiazine was better than 2% of the agent (commonly clinically used; compare FIG. 6C and below) and could be improved by the addition of either 0.25% or 0.5% zinc pyrithione (below). More specifically, 1% silver sulfadiazine completely eliminated detectable bacterial burden in 5 of 10 animals (50% treated), whereas combinations of 1% silver sulfadiazine and 0.25% or 0.5% eliminated *A. baumannii* from 7 (70%) or 10 (100%) of animals tested.

From these perspectives, a combination ointment containing ≤2% silver sulfadiazine and ≤2% zinc pyrithione is superior to that of 2% silver sulfadiazine alone.

What is claimed is:

1. A composition comprising zinc pyrithione and silver sulfadiazine wherein the weight ratio between zinc pyrithione and silver sulfadiazine is from 1:4 to 1:2, wherein the total concentration of silver sulfadiazine is 1 wt. %, and wherein the total concentration of zinc pyrithione is from 0.25 wt. % to 0.5 wt. %.

2. The composition of claim 1, wherein the composition is for topical administration to a subject.

3. The composition of claim 2, wherein the subject has microbial infection.

4. The composition of claim 3, wherein the microbial infection is bacterial infection.

5. The composition of claim 1, wherein the weight ratio between zinc pyrithione and silver sulfadiazine is 1:4.

6. The composition of claim 1, wherein the weight ratio between zinc pyrithione and silver sulfadiazine is 1:2.

7. A topical formulation comprising zinc pyrithione, silver sulfadiazine, and one or more pharmaceutically acceptable carriers or excipients wherein the weight ratio between zinc pyrithione and silver sulfadiazine is from 1:4 to 1:2, wherein the total concentration of silver sulfadiazine is 1 wt. %, and wherein the total concentration of zinc pyrithione is from 0.25 wt. % to 0.5 wt. %.

8. The topical formulation of claim 7, wherein the formulation is in the form of a cream, a lotion, an ointment, a hydrogel, a colloid, a gel, a foam, an oil, a milk, a suspension, a wipe, a sponge, a solution, an emulsion, a paste, a patch, a pladget, a swab, a dressing, a spray and a pad.

9. A method of decolonizing a microbial organism comprising contacting the microbial organism with a composition according to claim 1 wherein the microbial organism is *Acinetobacter baumannii, Pseudomonas aeruginosa* or *Staphylococcus aureus*.

10. A method of destroying or disrupting or inhibiting or reducing biofilm formation of a microbial organism comprising contacting the microbial organism with a composition according to claim 1 wherein the microbial organism is *Acinetobacter baumannii, Staphylococcus aureus* or *Pseudomonas aeruginosa*.

11. A method of treating a microbial infection in a subject comprising administering to the subject a therapeutically effective amount of the composition of claim 1 wherein the infection is *Acinetobacter baumannii, Staphylococcus aureus* or *Pseudomonas aeruginosa*.

12. The method of claim 11, wherein the bacterial infection is characterized by colonization of a bacterium.

13. The method of claim 11, wherein the bacterial infection is characterized by biofilm formation.

14. The method of claim 11, wherein the microbial infection is a topical infection.

15. The method of claim 14, wherein the topical infection is selected from wound, ulcer and lesion.

16. The composition of claim 4, wherein the bacterial infection is a gram-negative or gram-positive bacterial infection.

17. The composition of claim 4, wherein the bacterial infection is an *Acinetobacter baumannii, Pseudomonas aeruginosa* or *Staphylococcus aureus* infection.

18. The topical formulation of claim 7, wherein the formulation is for administration to a subject with a gram-negative or gram-positive bacterial infection.

19. The topical formulation of claim 7, wherein the formulation is for administration to a subject with an *Acinetobacter baumannii, Pseudomonas aeruginosa* or *Staphylococcus aureus* infection.

* * * * *